United States Patent
Furukawa

(10) Patent No.: US 11,035,061 B2
(45) Date of Patent: Jun. 15, 2021

(54) DECORATIVE SHEET AND METHOD FOR MANUFACTURING SAME

(71) Applicant: ZUIKO CORPORATION, Osaka (JP)

(72) Inventor: Daisuke Furukawa, Osaka (JP)

(73) Assignee: ZUIKO CORPORATION, Osaka (JP)

(*) Notice: Subject to any disclaimer, the term of this patent is extended or adjusted under 35 U.S.C. 154(b) by 0 days.

(21) Appl. No.: 16/486,251

(22) PCT Filed: Feb. 26, 2018

(86) PCT No.: PCT/JP2018/006908
§ 371 (c)(1),
(2) Date: Aug. 15, 2019

(87) PCT Pub. No.: WO2018/163879
PCT Pub. Date: Sep. 13, 2018

(65) Prior Publication Data
US 2019/0368090 A1    Dec. 5, 2019

(30) Foreign Application Priority Data

Mar. 7, 2017    (JP) .............................. JP2017-042909

(51) Int. Cl.
*B32B 3/00*    (2006.01)
*D04H 1/54*    (2012.01)

(52) U.S. Cl.
CPC ......... *D04H 1/54* (2013.01); *D10B 2401/061* (2013.01)

(58) Field of Classification Search
CPC ........................... D04H 1/54; D01B 2401/061
See application file for complete search history.

(56) References Cited

U.S. PATENT DOCUMENTS

| 4,333,979 A | 6/1982 | Sciaraffa et al. |
| 4,592,943 A | 6/1986 | Cancian et al. |

(Continued)

FOREIGN PATENT DOCUMENTS

| EP | 1959037 A1 | 8/2008 |
| EP | 2881096 A1 | 6/2015 |

(Continued)

OTHER PUBLICATIONS

International Search Report Issued in PCT/JP2018/006908 dated Mar. 27, 2018.

(Continued)

*Primary Examiner* — Elizabeth E Mulvaney
(74) *Attorney, Agent, or Firm* — Renner, Otto, Boisselle & Sklar, LLP

(57) ABSTRACT

A shaped sheet including a plurality of rows of protruding portions formed on a non-woven fabric sheet and extending in a first direction and a plurality of rows of protruding portions formed on the non-woven fabric sheet and extending in a second direction that crosses the first direction, wherein: the shaped sheet is more stretchable in the first direction than in the second direction; the shaped sheet is formed from a single layer of the non-woven fabric sheet; and a fusion-bonded portion that extends discontinuously or continuously in the first direction and that has a smaller thickness than the protruding portions due to its fusion-bonded structure is provided along a part or whole of a periphery of the protruding portions on the shaped sheet.

8 Claims, 10 Drawing Sheets

(56) References Cited

U.S. PATENT DOCUMENTS

| | | |
|---|---|---|
| 6,955,847 B1 | 10/2005 | Itou et al. |
| 2016/0075122 A1 | 3/2016 | Strube et al. |
| 2017/0319399 A1* | 11/2017 | Desai .................... B32B 3/10 |
| 2018/0140478 A1 | 5/2018 | Fukuhara |

FOREIGN PATENT DOCUMENTS

| | | |
|---|---|---|
| JP | S59-88959 A | 5/1984 |
| JP | 2004-113489 A | 4/2004 |
| JP | 2004-174234 A | 6/2004 |
| WO | WO 01/11130 A1 | 2/2001 |
| WO | WO 01/47697 A1 | 7/2001 |
| WO | WO 2008/129138 A1 | 10/2008 |
| WO | WO 2008/146594 A1 | 12/2008 |
| WO | WO 2016/199543 A1 | 12/2016 |

OTHER PUBLICATIONS

Extended European Search Report for corresponding EP Application No. 18763161.9 dated Nov. 18, 2020.

\* cited by examiner

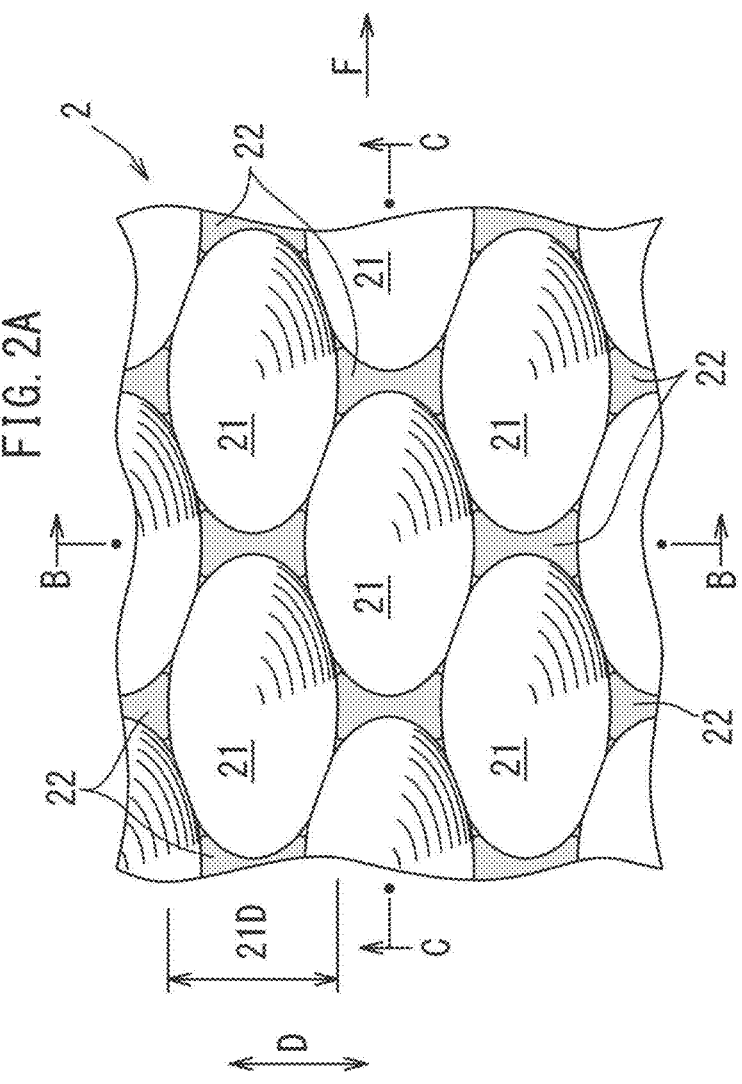
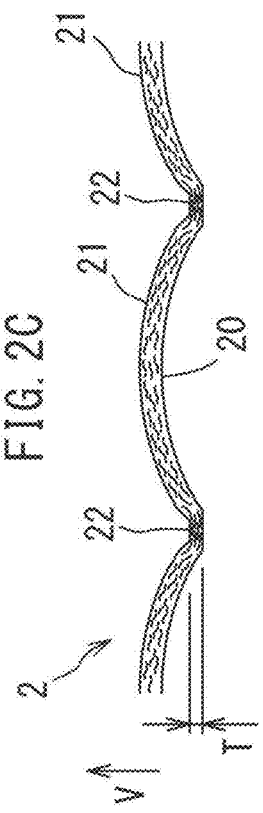
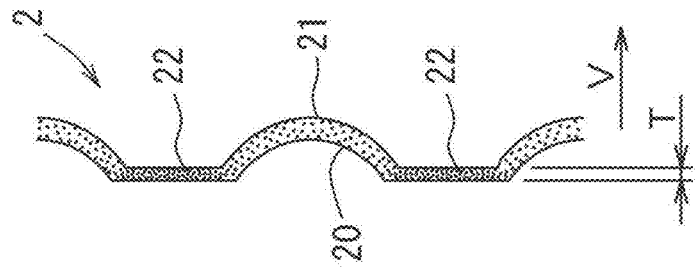

form a single layer of the non-woven fabric sheet 1 is conveyed
DECORATIVE SHEET AND METHOD FOR MANUFACTURING SAME

TECHNICAL FIELD

The present invention relates to a decorative sheet (shaped sheet) obtained by shaping a single-layer non-woven fabric sheet, and a method for manufacturing the same.

BACKGROUND ART

With the conventional technique disclosed in JP2004-174234A, a shaped sheet, which is obtained by shaping a plurality of protruding portions on a non-woven fabric sheet, and a flat sheet are intermittently attached together along the periphery of the protruding portions, so as to maintain the shape of the obtained protruding portions.

CITATION LIST

Patent Literature

First Patent Document: JP2004-174234A (front page)
Second Patent Document: WO2016/199543A1 (front page)

SUMMARY OF INVENTION

However, such a shaped sheet requires two sheets, thereby resulting in a high cost.

Moreover, such a two-layer shaped sheet will cause worn articles such as disposable diapers and sanitary products, for example, to be bulky.

Thus, it is an object of the present invention to provide a shaped sheet that is inexpensive and prevented from being bulky and with which it is possible to maintain the shape of the protruding portions, and a method for manufacturing the same.

A shaped sheet of the present invention is a shaped sheet 2 including a plurality of rows of protruding (convex) portions 21 formed on a non-woven fabric sheet 1 and extending in a first direction D and a plurality of rows of protruding (convex) portions 21 formed on the non-woven fabric sheet 1 and extending in a second direction F that crosses the first direction D, wherein:

the shaped sheet 2 is more stretchable in the first direction D than in the second direction F;

the shaped sheet 2 is formed from a single layer of the non-woven fabric sheet 1; and a fusion-bonded portion 22 that extends discontinuously or continuously in the first direction D and that has a smaller thickness than the protruding portions 21 due to its fusion-bonded structure is provided along a part or whole of a periphery of each of the protruding portions 21 on the shaped sheet 2.

A method for manufacturing a shaped sheet of the present invention is a method for manufacturing a shaped sheet 2 including a plurality of rows of protruding (convex) portions 21 formed on a non-woven fabric sheet 1 and extending in a first direction D and a plurality of rows of protruding (convex) portions 21 formed on the non-woven fabric sheet 1 and extending in a second direction F that crosses the first direction D, the method comprising:

a step of conveying a single layer of the non-woven fabric sheet 1, which is more stretchable in a width direction than in a longitudinal direction, in the longitudinal direction;

a shape-giving step of shaping the plurality of rows of protruding portions 21 on the non-woven fabric sheet 1 being conveyed; and a fusion-bonding step of forming a fusion-bonded portion 22, where constituent fibers 11 of the single-layer non-woven fabric sheet 1 are fusion-bonded together, along a part or whole of a periphery of the protruding portions 21 on the single-layer non-woven fabric sheet 1 or the shaped sheet 2.

According to the present invention, the fusion-bonded portions 22 are formed by fusion-bonding together the constituent fibers 11 of the single-layer non-woven fabric sheet 1, which is more stretchable in the width direction than in the longitudinal direction. The fusion-bonded portions 22 are formed by a fusion-bonded structure that has a smaller thickness than the protruding portions 21 of the shaped sheet 2. Such fusion-bonded portions 22 are harder and have a higher rigidity than the protruding portions 21.

Therefore, the fusion-bonded portions 22 will inhibit the stretch of the shaped sheet 2 in the first direction D, in which the shaped sheet 2 is more stretchable, along the periphery of the protruding portions. Therefore, the protruding portions are less likely to collapse, and it is possible, even with a single-layer sheet, to maintain the shape of the protruding portions. As a result, it is possible to obtain a shaped non-woven fabric sheet that is inexpensive. Moreover, it is possible to prevent the shaped sheet from being bulky.

BRIEF DESCRIPTION OF DRAWINGS

FIG. 1 shows ridgelines on protruding portions so as to make it easier to understand the protruding shape.

FIG. 2A is a super-enlarged plan view showing a portion of the shaped sheet as seen from the front surface, FIG. 2B is a cross-sectional view taken along line B-B of FIG. 2A, and FIG. 2C is a cross-sectional view taken along line C-C of FIG. 2A.

In FIG. 1 to FIG. 5B, fusion-bonded portions are colored in gray.

Figure 3:
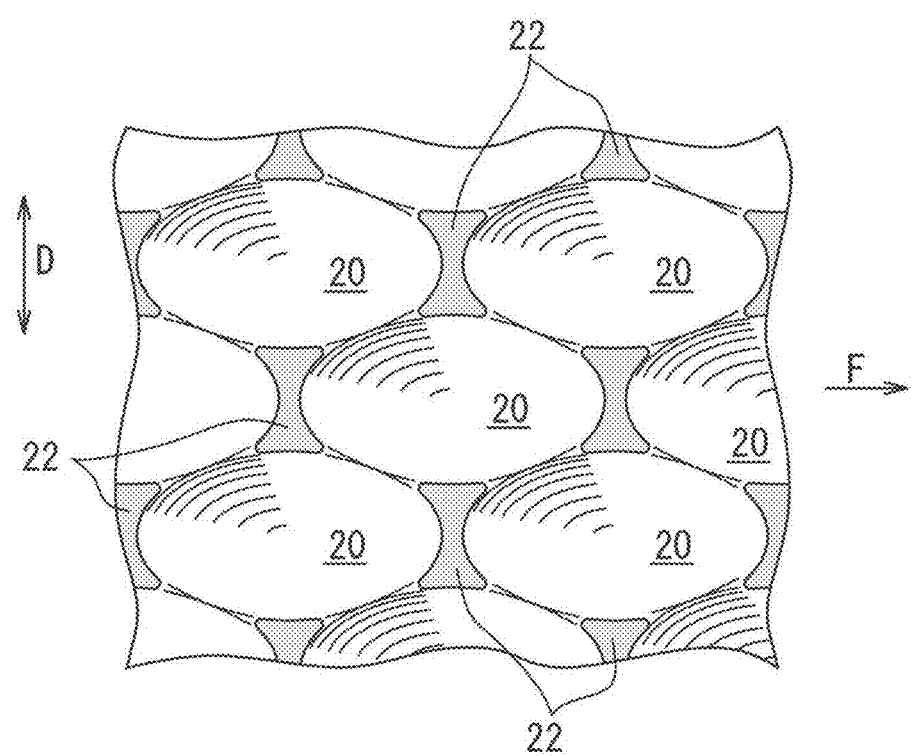
FIG. 3 is a super-enlarged plan view showing a portion of the shaped sheet as seen from the back surface.

The protruding portions of FIG. 2A and the depressed (concave) portions of FIG. 3 are shaded assuming that they are illuminated from the upper-left direction.

Figure 6:
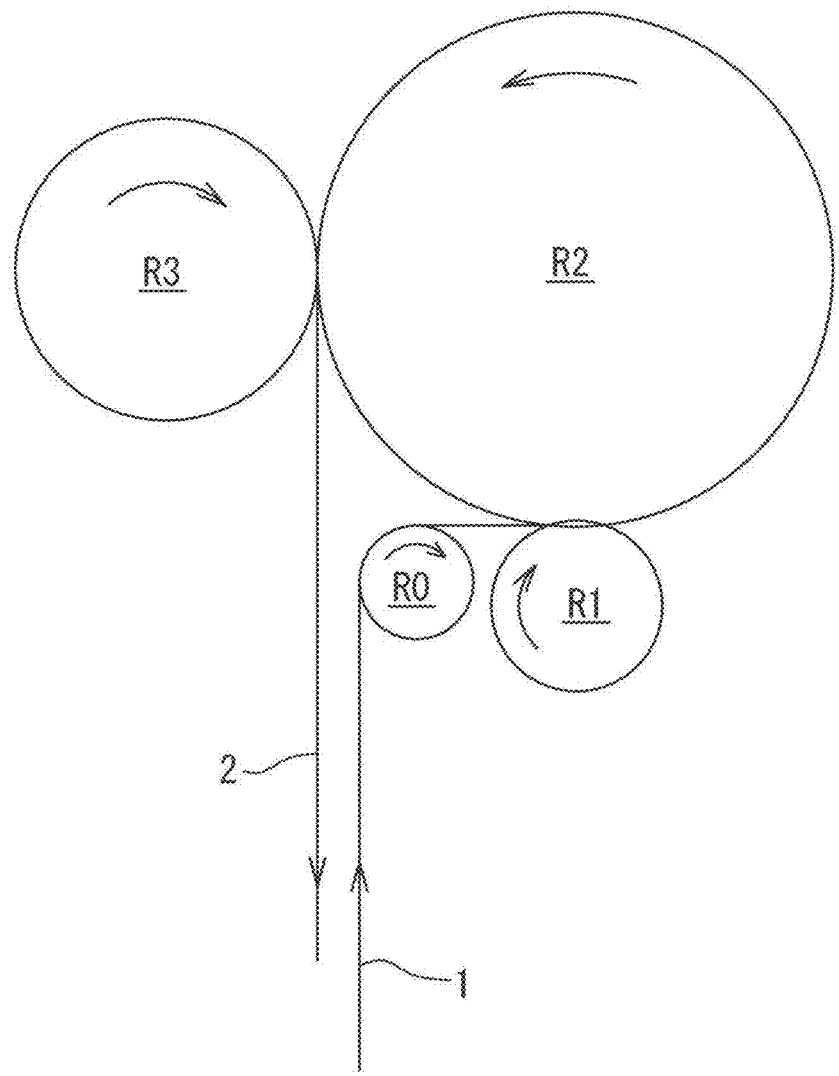

FIG. 6 is a layout diagram showing an example of a manufacturing apparatus.

Figure 7A:
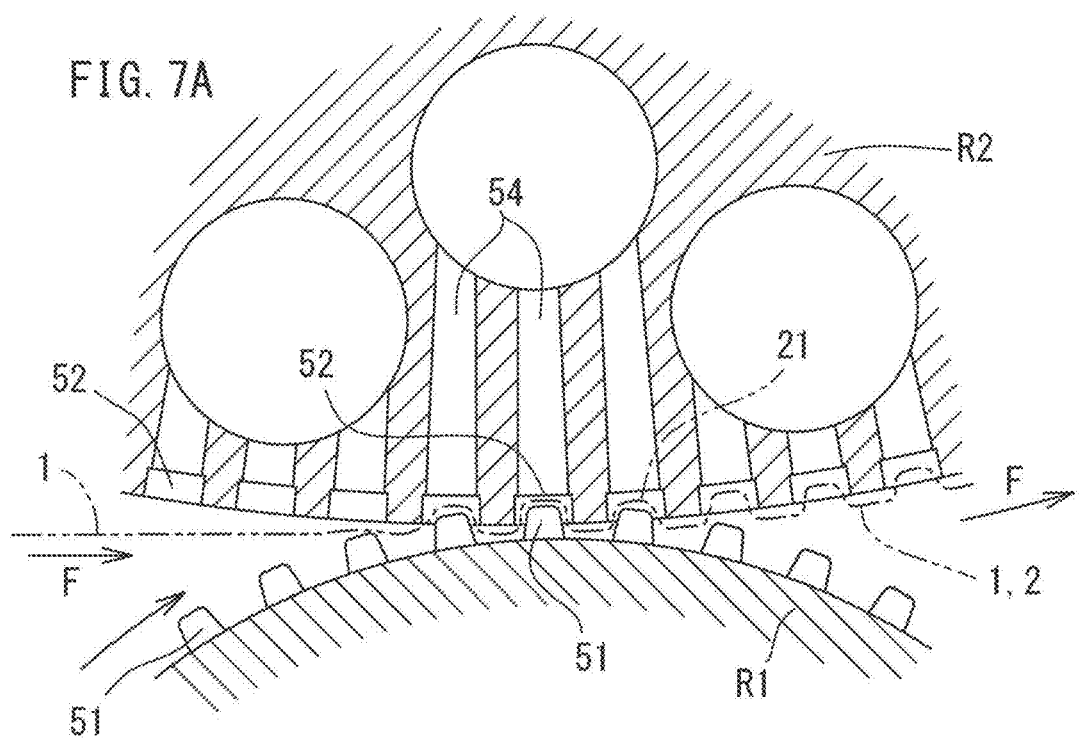
Figure 7B:
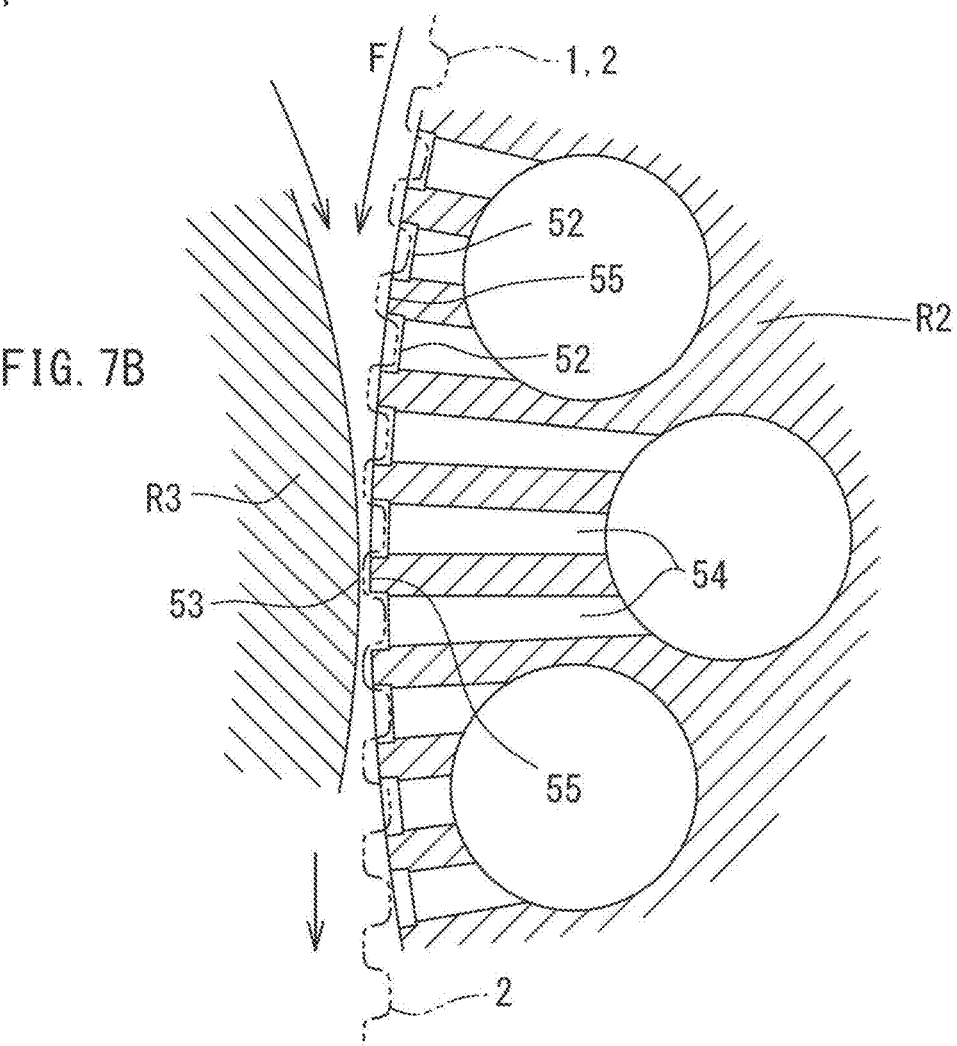

FIG. 7A is an enlarged cross-sectional view showing a portion of a first roll and a portion of a second roll, and FIG. 7B is an enlarged cross-sectional view showing a portion of the second roll and a portion of a third roll.

Figure 8A:
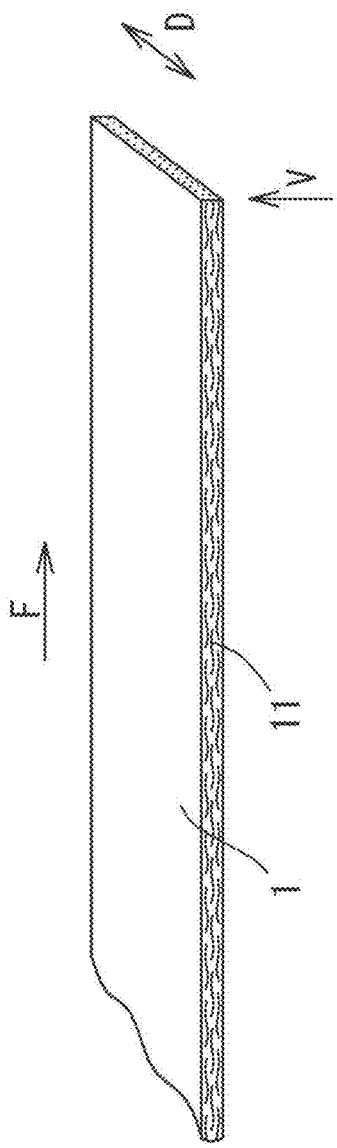
Figure 8B:
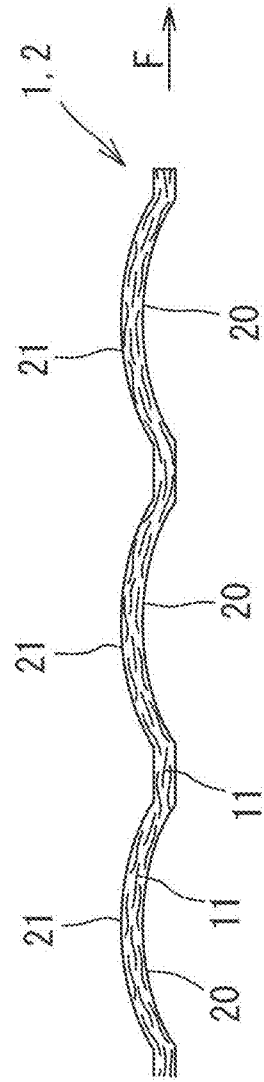
Figure 8C:
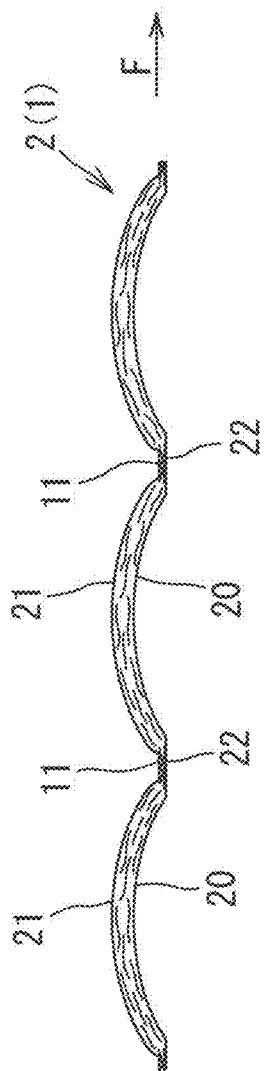

FIG. 8A, FIG. 8B and FIG. 8C are a super-enlarged perspective view and super-enlarged cross-sectional views, respectively, showing a manufacturing method.

Figure 9A:
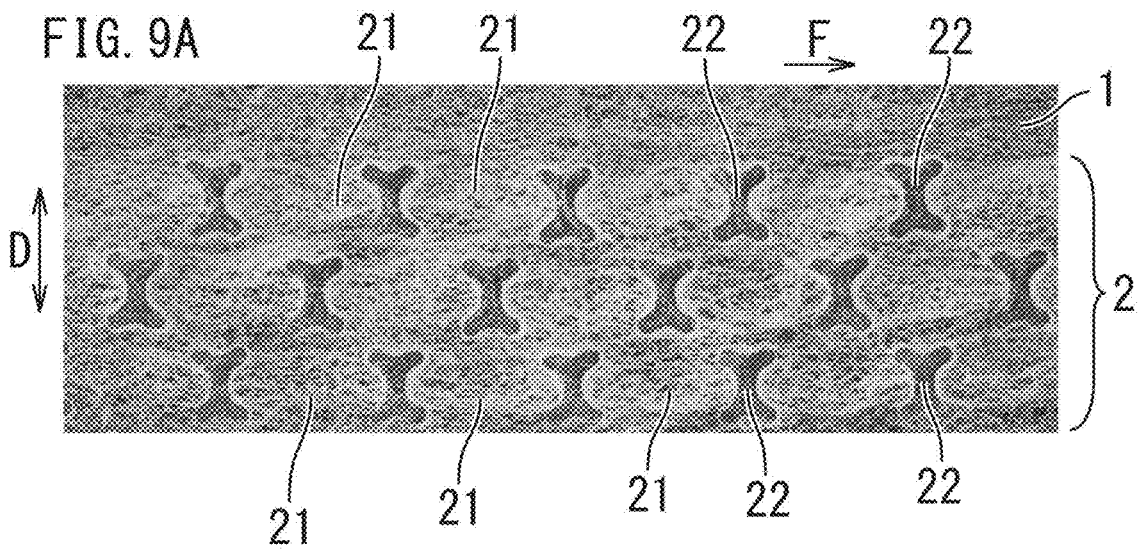
Figure 9B:
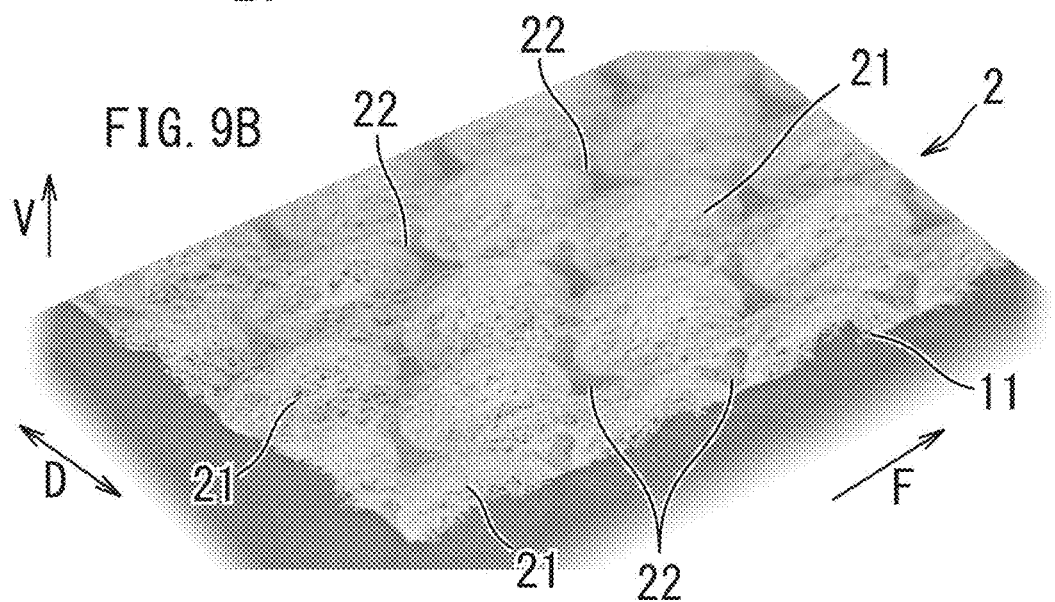
Figure 9C:
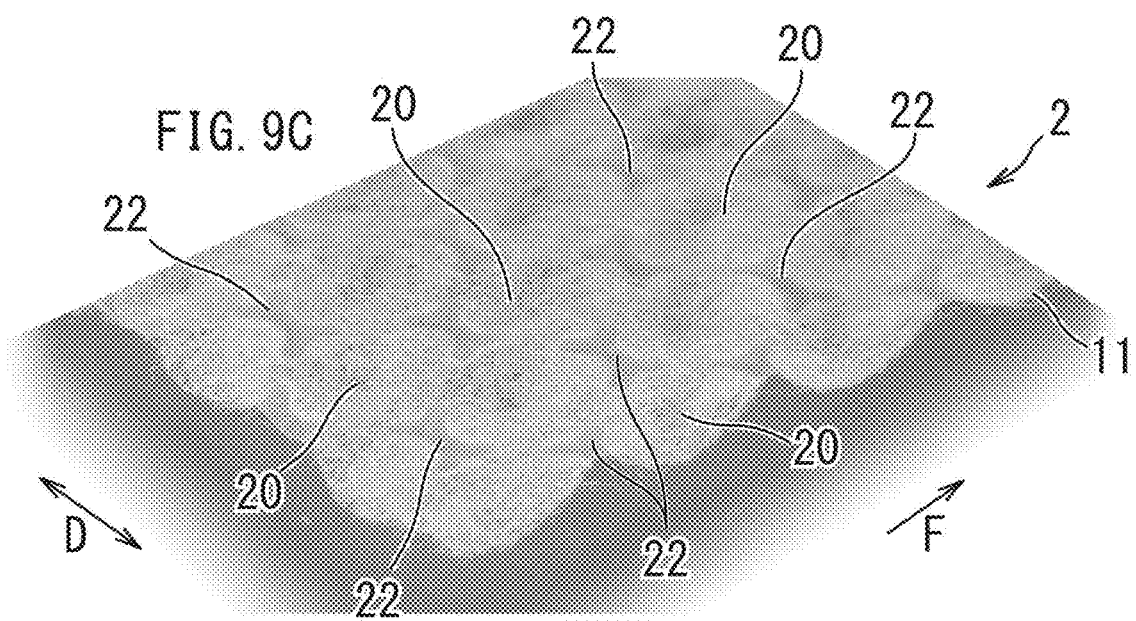

FIG. 9A is an enlarged plan view showing a digital photograph of a portion of a shaped sheet including a non-woven fabric sheet portion along its edge portion, FIG. 9B is an enlarged perspective view showing a digital photograph of a portion of the shaped sheet taken from the front surface, and FIG. 9C is an enlarged perspective view showing a digital photograph of a portion of the shaped sheet taken from the back surface.

Figure 10A:
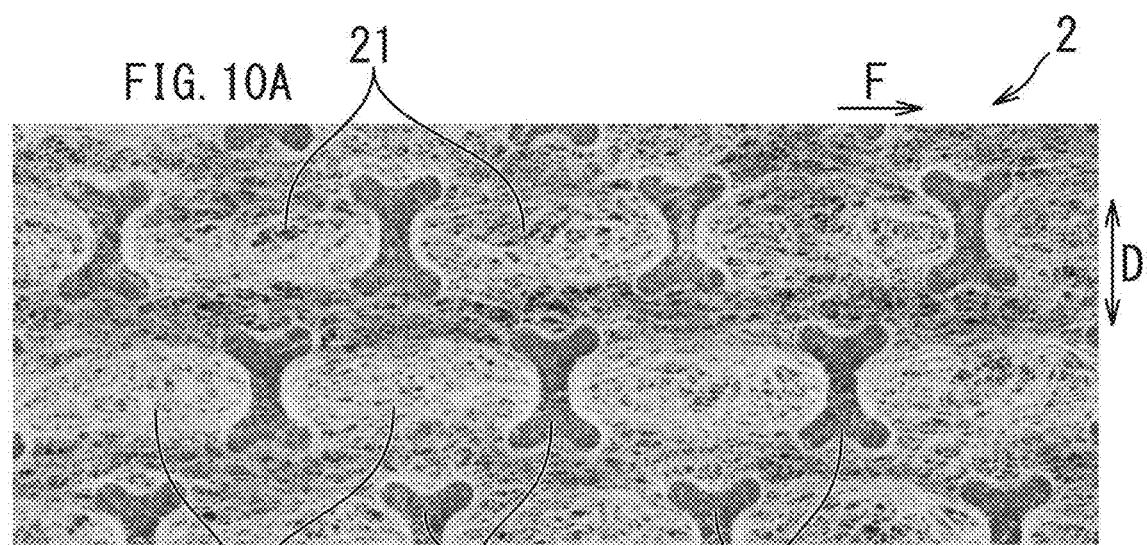
Figure 10B:
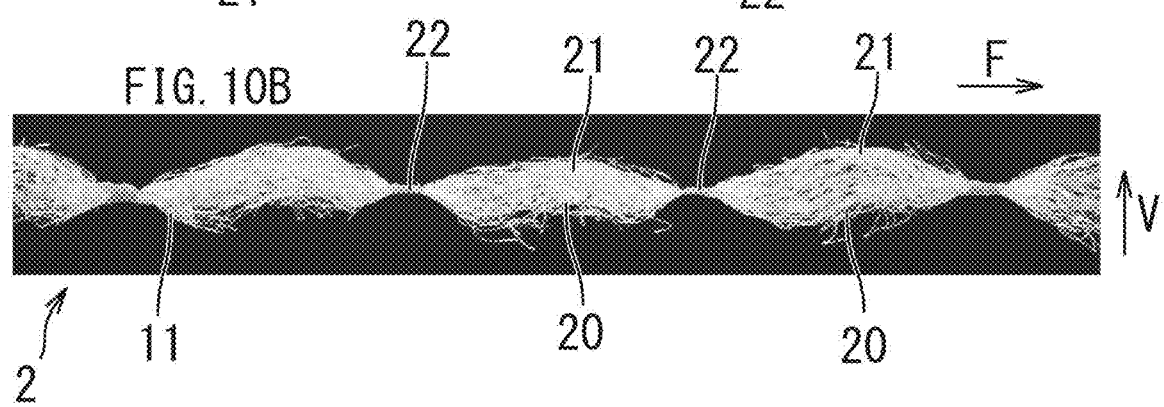
Figure 10C:
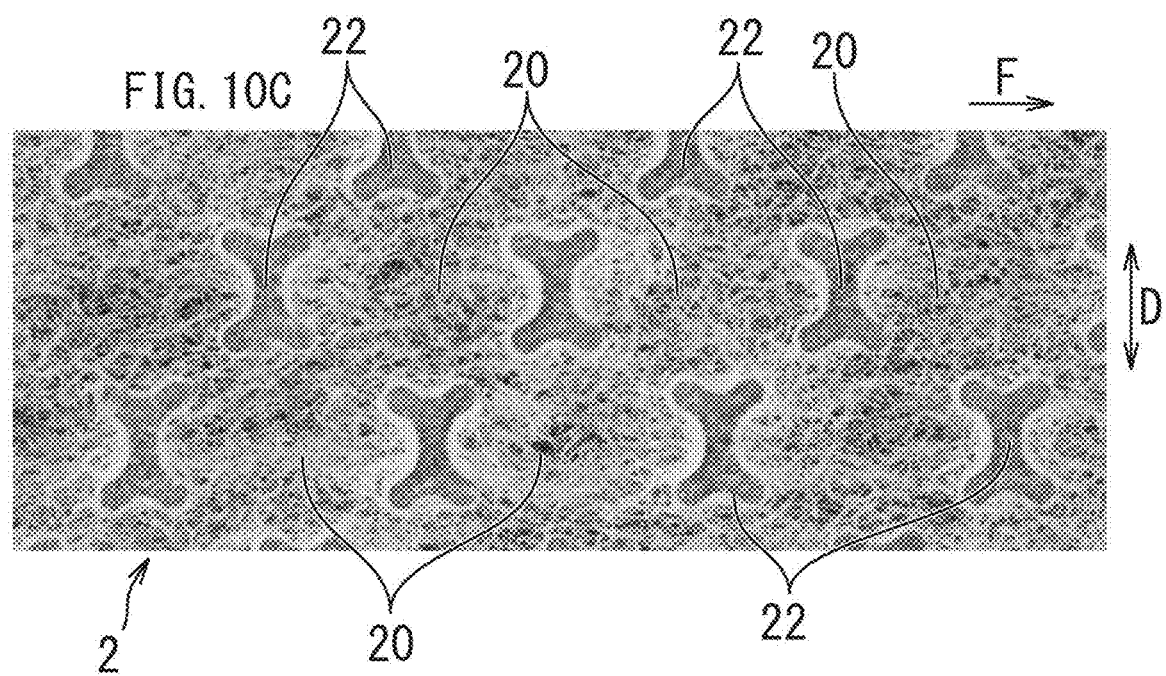

FIG. 10A is a super-enlarged plan view showing a digital photograph of a portion of a shaped sheet taken from the front surface. FIG. 10B is a super-enlarged cross-sectional view showing a slice of the shaped sheet taken from the side, and FIG. 10C is a super-enlarged bottom view showing a digital photograph of a portion of the shaped sheet taken from the back surface.

DESCRIPTION OF EMBODIMENTS

In a preferred embodiment, the fusion-bonded portion 22 of the shaped sheet is formed by the fusion-bonded structure where constituent fibers 11 of the single-layer non-woven fabric sheet 1 are fusion-bonded together.

The constituent fibers 11 of the single-layer non-woven fabric sheet 1 being fusion-bonded together means that the fusion-bonded portion 22 is not substantially fusion-bonded to other non-woven fabrics. Also, this does not refer to a fusion bond between two layers of a folded portion of the non-woven fabric sheet 1 that is folded in two.

Such a fusion-bonded portion is harder and has a higher rigidity than non-fusion-bonded portions such as the protruding portions. Thus, it is possible to inhibit the stretch of the shaped sheet 2 in the first direction along the periphery of the protruding portions.

Note that the size of each fusion-bonded portion is very small, and it is believed to be difficult to objectively measure the hardness and the rigidity thereof. Thus, the fusion-bonded portions are defined by the thickness.

As for the method for measuring the thickness, the thickness can be measured by a method in accordance with JIS L1913. Typically, however, by enlarging a section of a shaped sheet using a digital camera, a microscope, or the like, it is possible to easily observe the difference between the thickness of the fusion-bonded portions and the thickness of the protruding portions.

In a preferred embodiment, the fusion-bonded portion 22 of the shaped sheet includes a central portion 23 that is between protruding portions 21 that are adjacent to each other in the first direction D, and the fusion-bonded portion 22 extends at least in one direction along the first direction D from the central portion 23.

Adjacent protruding portions are close to each other at the central portion, and this is likely the most stretchable area. In view of this, with the fusion-bonded portion including the central portion and extending in the first direction, the shaped sheet 2 is less stretchable in the first direction.

In a preferred embodiment, the shaped sheet has a fiber density of constituent fibers that is higher in the fusion-bonded portions 22 than in the protruding portions 21.

The fiber density refers to the mass of constituent fibers per unit volume of the shaped sheet. The fiber density being high means that there is a large amount of constituent fibers existing per unit volume of the sheet. The fiber density being low means that there is a small amount of constituent fibers existing per unit volume of the sheet.

As for the method for measuring the fiber density, a section of the sheet may be observed on an enlarged scale using a scanning electron microscope so as to count the number of constituent fibers that are cut along the section per unit area (about 0.5 mm$^2$).

Such fusion-bonded portions 22 are harder and have a higher rigidity than the protruding portions 21. Therefore, the fusion-bonded portions 22 will inhibit the stretch in the first direction, in which the shaped sheet 2 is more stretchable, along the periphery of the protruding portions.

Note that with shaped sheets where the fusion-bonded portions 22 are made into a film form to such a degree that the fusion-bonded portions 22 are nearly transparent, there may be cases where it is not possible to clearly observe the existence of constituent fibers in the fusion-bonded portions 22, and the fiber density in the fusion-bonded portions 22 is lower than that in the protruding portions 21.

In a preferred embodiment, a rate of elongation of the shaped sheet when pulled in the first direction D is smaller in the fusion-bonded portions 22 than in the protruding portions 21.

The method for measuring the rate of elongation may be a method in accordance with JIS L1913. It may be possible to observe, with a microscope, or the like, that the protruding portions 21 stretch while the fusion-bonded portions 22 do not substantially stretch when the shaped sheet is pulled at a low velocity in the first direction D. In such a case, it may rupture at the boundary between the protruding portion 21 and the fusion-bonded portion 22.

Such fusion-bonded portions 22 are harder and have a higher rigidity than the protruding portions 21. Therefore, the fusion-bonded portions 22 will inhibit the stretch of the shaped sheet 2 in the first direction D, in which the shaped sheet 2 is more stretchable, along the periphery of the protruding portions.

As a result of constituent fibers being fusion-bonded together along the fusion-bonded portions 22 of the shaped sheet 2, the fusion-bonded portions 22 will be less stretchable equally in the first direction D and in the second direction F. On the other hand, the non-fusion-bonded protruding portions 21 are more stretchable in the first direction D. Therefore, the shaped sheet 2 as a whole is more stretchable in the first direction D than in the second direction F. In such a case, it can be said that "the shaped sheet 2 is more stretchable in the first direction D than in the second direction F".

Therefore, "the shaped sheet 2 is more stretchable in the first direction D than in the second direction F" means, for example, that the shaped sheet 2 of such a size that many protruding portions 21 and many fusion-bonded portions 22 are included is more stretchable in the first direction D than in the second direction F as a result of the comparison between when the shaped sheet 2 as a whole is pulled in the first direction D and when the shaped sheet 2 as a whole is pulled in the second direction F.

In the present invention, the individual protruding portions 21 and the individual fusion-bonded portions 22 are very small, and it is difficult to determined whether each protruding portion 21 or each fusion-bonded portion 22 is more stretchable in the first direction D. Therefore, the stretchability is defined based on the stretchability of the shaped sheet 2 including the protruding portions 21 and the fusion-bonded portions 22.

That is, the method for determining whether "the shaped sheet 2 is more stretchable in the first direction D than in the second direction F" may be a method in accordance with JIS L1913 mentioned above.

In a preferred manufacturing method:

in the shape-giving step, a first roll R1 and a second roll R2 mesh with each other, thereby shaping the non-woven fabric sheet 1;

in the shape-giving step, the first and/or second roll R1, R2 are heated to a temperature range that is lower than a melting point of the constituent fibers 11 of the non-woven fabric sheet 1; and the fusion-bonding step is performed as a heating device R3 comes into contact with the second roll R2 with the fusion-bonded portion 22 of the non-woven fabric sheet 1 interposed therebetween.

In such a case, it becomes easier to shape the protruding portions 21 on the non-woven fabric sheet 1, and it is possible to suppress the formation of through holes running through the shaped sheet in the fusion-bonded portions 22.

Note that although the heating device is preferably a heating roll, it may be an ultrasonic heating device.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

An embodiment of the present invention will now described with reference to the drawings.

Figure 1:
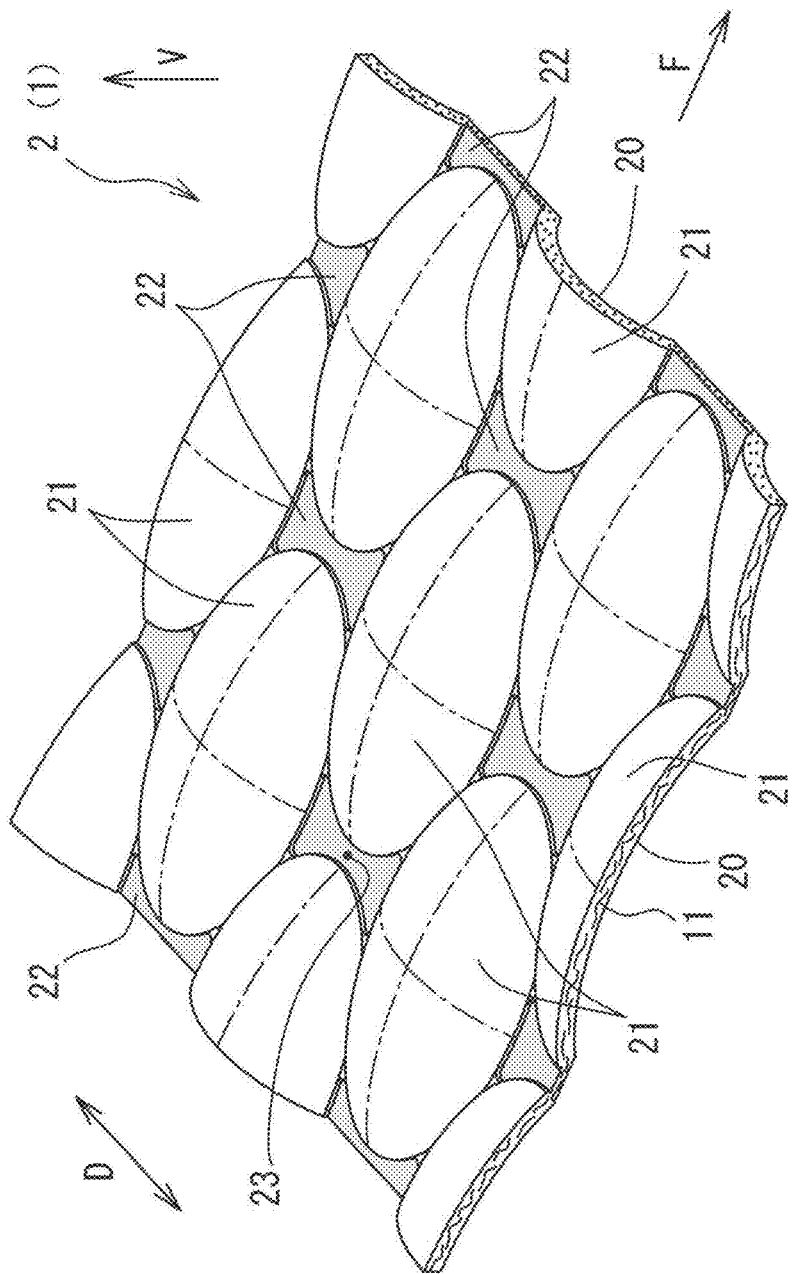
FIG. 1 is a super-enlarged perspective view of Embodiment 1, showing a portion of a shaped sheet of the present invention on an about 10 times enlarged scale.

As shown in FIG. 1, a shaped sheet 2 is formed from a single-layer non-woven fabric sheet 1 and is used as the top sheet of the liquid-absorbing portion of a disposable worn article, for example. Therefore, the shaped sheet 2 has a predetermined liquid permeability and a predetermined air permeability.

As shown in FIG. 1, the shaped sheet 2 includes a plurality of rows of protruding portions 21 formed on the non-woven fabric sheet 1 and extending in the first direction D, and a plurality of rows of protruding portions 21 formed on the non-woven fabric sheet 1 and extending in the second direction F that crosses the first; direction D.

Note that many protruding portions 21 may be formed across the entire width of the non-woven fabric sheet 1, or the side edge portion of the non-woven fabric sheet 1 may be left unprocessed, i.e., as the original non-woven fabric with no protruding portions thereon as shown in FIG. 9A.

While the first direction D coincides with the width direction of the continuous non-woven fabric sheet 1 of FIG. 8A in the present embodiment, the first direction D may be slightly inclined relative to the width direction. The constituent fibers of the non-woven fabric sheet 1 of the present embodiment are longer in the second direction F than in the first direction D, and the shaped sheet 2 is therefore more stretchable in the first direction D than in the second direction F.

As shown in FIG. 2A to FIG. 2C, in the present embodiment, the second direction F crosses the first direction D so as to be orthogonal to the first direction D, but the second direction F may cross the first direction D with an inclination relative to the first direction D.

Fusion-bonded portions 22 are provided on the shaped sheet 2 of FIG. 1. The fusion-bonded portions 22 have a thickness T of FIG. 2B that is thinner than the protruding portions 21 due to the fusion-bonded structure. That is, as shown in FIG. 2B and FIG. 2C, on the single-layer shaped sheet 2, the protruding portions 21 and the fusion-bonded portions 22, which have a thickness T that is thinner than the protruding portions 21, are arranged alternating with each other in the first direction D and in the second direction F.

As shown in FIG. 2B and FIG. 2C, the fiber density of constituent fibers may be higher in the fusion-bonded portions 22 than in the protruding portions 21. Moreover, the rate of elongation of the shaped sheet when pulled in the first direction D may be smaller in the fusion-bonded portions 22 than in the protruding portions 21.

In the present embodiment, the fusion-bonded portions 22 of FIG. 1 are provided along a part of the periphery of each protruding portion 21 of the shaped sheet 2. When the fusion-bonded portions 22 are provided along a part of the periphery, the fusion-bonded portions 22 extend discontinuously in the first direction D.

Figure 4A:
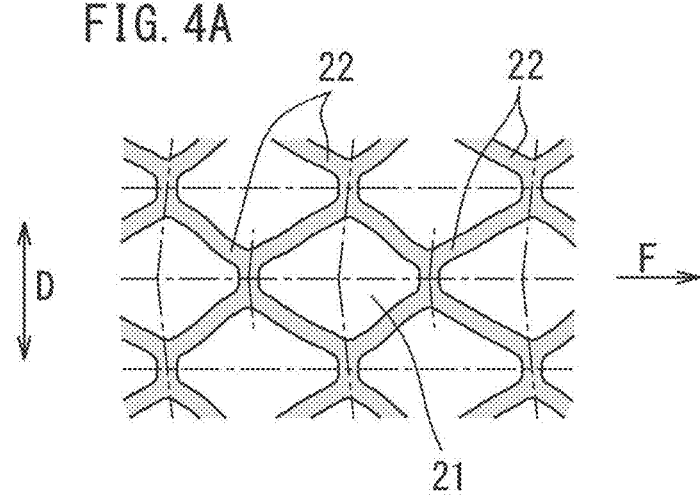
FIG. 4A and FIG. 4B are enlarged plan views showing patterns of fusion-bonded portions.

As shown in FIG. 4A, the fusion-bonded portions 22 may be provided along the whole of the periphery of each protruding portion 21 of the shaped sheet 2. When the fusion-bonded portions 22 are provided along the whole of the periphery, the fusion-bonded portions 22 extend continuously in the first direction D and in the second direction F, thereby forming a loop shape.

As shown in FIG. 8B, FIG. 8C and FIG. 10B, constituent fibers 11 of the single-layer non-woven fabric sheet 1 are fusion-bonded together in the fusion-bonded portions 22 formed by the fusion-bonded structure. The fusion-bonded portions 22 of FIG. 1 formed by the fusion-bonded structure inhibit the stretch of the shaped sheet 2 in the first direction D.

The fusion-bonded portions 22 where the constituent fibers 11 are fusion-bonded together has a higher transparency than the protruding portions 21 as clearly shown in FIG. 9A, and is semi-transparent. Typically, the transparency can be visually observed.

Transparency as used herein is a measure of transparentness of a substance or a material, and the degree of transparentness may be expressed by the light transmittance, for example.

As the method for measuring the transparency, it is possible to measure the transparency by using a haze meter, or the like. Specifically, a test piece can be cut out so as to measure the transparency referring to JIS K 7136 (plastics—determination of haze of transparent materials).

The shaped sheet 2 is formed from the single-layer non-woven fabric sheet 1.

The non-woven fabric sheet 1 may be a non-woven fabric formed from an air-through non-woven fabric (thermal bond non-woven fabric) or a water-entangled water-punched non-woven fabric. The constituent fibers 11 of these non-woven fabrics are fusion-bonded together, thereby forming the fusion-bonded structure of the fusion-bonded portions 22.

The basis weight (grammage) of the non-woven fabric sheet 1 is preferably about 25 to about 50 g/m². When the basis weight is less than 25 g/m², it will be difficult, with a single-layer non-woven fabric sheet 1, to maintain the shape of the protruding portions 21. On the other hand, when the basis weight is greater than 50 g/m², it may increase the cost and deteriorate the feel even with a single-layer non-woven fabric sheet 1. More preferably, the basis weight is about 30 to about 40 g/m².

In FIG. 1, the fusion-bonded portion 22 may include a central portion 23 that is between protruding portions 21 that are adjacent to each other in the first direction D, and the fusion-bonded portion 22 may extend at least in one direction along the first direction D from the central portion 23. In FIG. 1, the fusion-bonded portion 22 is formed so as to be longer in the first direction D than in the second direction F. The fusion-bonded portion 22 may have a shape that is necked (constricted, or narrowed) in the central portion 23 (a bone shape, an hourglass shape).

As shown in FIG. 1, FIG. 4B, FIG. 5A and FIG. 5B, the fusion-bonded portions 22 may be provided intermittently and discontinuously in the first direction D along the periphery of the protruding portions 21. In these cases, the fusion-bonded portions 22 are provided intermittently and discontinuously also in the second direction F.

Figure 5A:
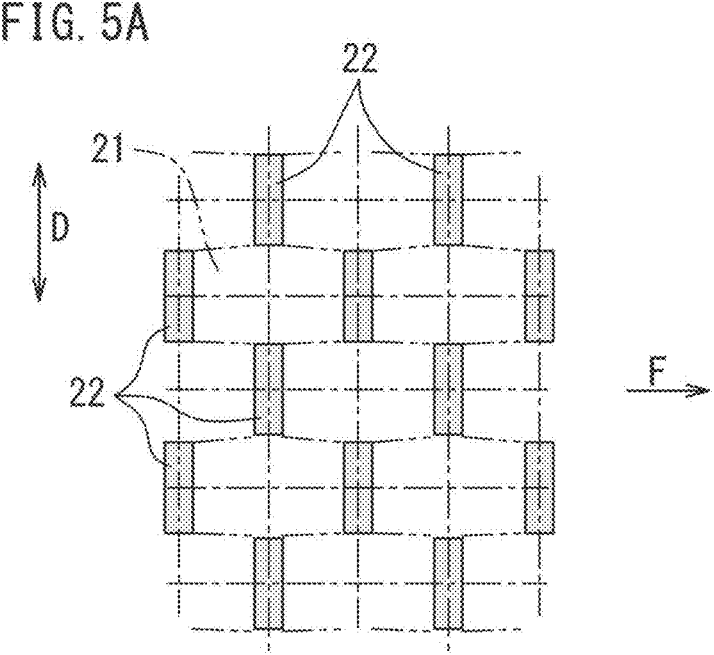
FIG. 5A and FIG. 5B are enlarged plan views showing other patterns of fusion-bonded portions.

As shown in FIG. 4A and FIG. 5A, the fusion-bonded portion 22 may be provided across the entire width of the protruding portion 21 in the first direction D. In the case of FIG. 5A, the fusion-bonded portions 22 are provided intermittently and discontinuously in the second direction. F.

As shown in FIG. 2A, the fusion-bonded portion 22 may be formed so as to extend in the first direction D across an area that is 60% or more of the width 21D of the protruding portion 21.

Figure 4B:
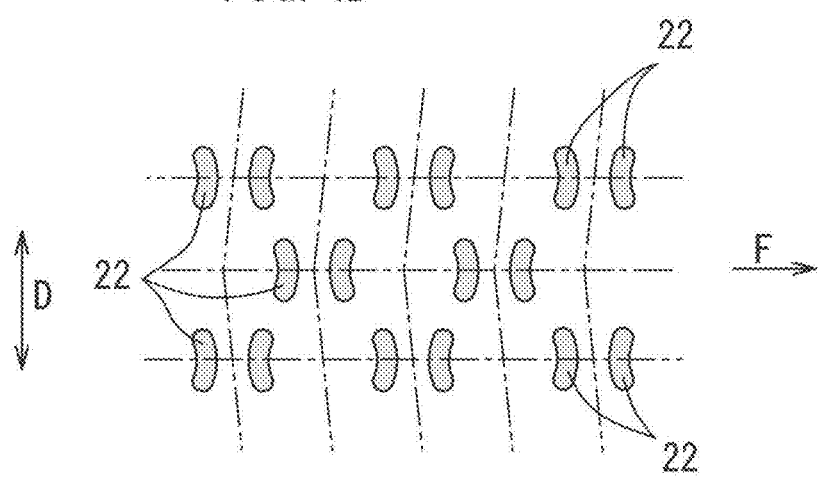
Figure 5B:
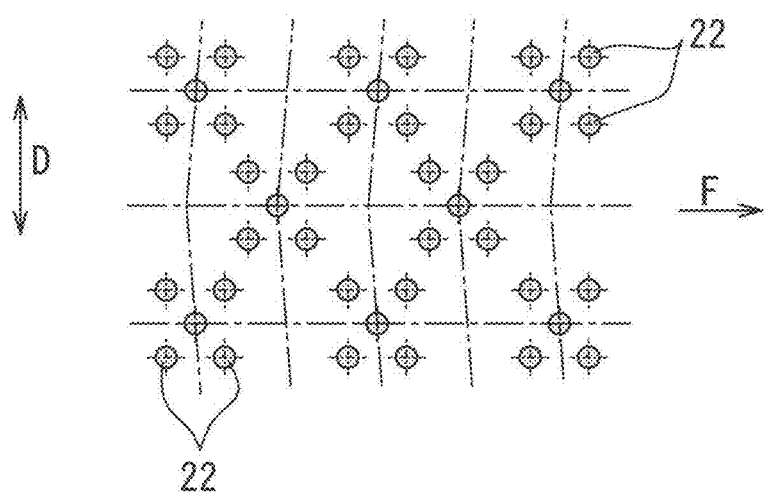

The planar shape of the fusion-bonded portion 22 may be any of various shapes such as the bone shape of FIG. 2A, the loop shape of FIG. 4A, the crescent shape of FIG. 4B, the rectangular shape of FIG. 5A or the dot shape of FIG. 5B.

A protruding surface is formed on the front surface of each protruding portion 21 of FIG. 1. A depressed surface is formed on the back surface of each protruding portion 21 as shown in FIG. 2B, FIG. 2C and FIG. 3.

While there is no particular limitation on the size of the protruding portions, it is typically often set to about 6 mm$^2$ to about 30 mm$^2$, and the height of the protruding portions is typically about 1 mm to about 5 mm, for use as the top sheet of a diaper, for example.

Next, a manufacturing apparatus will be briefly described.

As shown in FIG. 6, the manufacturing apparatus includes first to third rolls R1 to R3.

The first and second rolls R1, R2 of FIG. 6 mesh with each other so as to shape the non-woven fabric sheet 1, which is introduced from an introduction roll R0. As shown in FIG. 7A, the first roll R1 is provided with many shape-giving protruding portions 51. On the other hand, the second roll R2 is provided with many depressions 52. The protruding portions 51 and the depressions 52 mesh with each other so as to form the protruding portions 21 on the non-woven fabric sheet 1.

The depressions 52 of the second roll R2 of FIG. 7A are in communication with manifolds 54 for sucking the non-woven fabric sheet 1. The shaped non-woven fabric sheet 1 is sucked at the depressions 52, thereby maintaining the shape of the protruding portions 21.

The first and/or second roll R1, R2 of FIG. 7A may include a first heater (not shown). The first heater may be a heater and/or a hot air blower provided in the first and/or second roll R1, R2. The heater heats the first and/or second roll R1, R2 to a temperature range that is lower than the melting point of the constituent fibers 11 of the non-woven fabric sheet 1.

The second and third rolls R2, R3 of FIG. 7B are in contact with each other with the shaped non-woven fabric sheet 1 interposed therebetween. The second roll R2 has many fusion-bond protruding portions 55 between the depressions 52. The non-woven fabric sheet 1 is sandwiched between the protruding portions 55 and a surface 53 of the third roll R3.

The third roll (the heating device) R3 is heated by a heater (not shown) to a temperature range that is higher than the softening point or the melting point of the constituent fibers 11. Therefore, the temperature of the third roll R3 is higher than the temperature of the first and second rolls R1, R2.

Note that an ultrasonic heating device may be used instead of the third roll R3.

Next, a method for manufacturing the shaped sheet 2 will be described.

The single-layer non-woven fabric sheet 1, which is more stretchable in the width direction D than in the longitudinal direction F of FIG. 8A, is conveyed in the longitudinal direction F by the rolls R0 to R3 of FIG. 6. The first and second rolls R1, R2 of FIG. 7A shape the protruding portions 21 on the non-woven fabric sheet 1 being conveyed.

In this process, a plurality of rows of protruding portions 21 extending in the first direction D and a plurality of rows of protruding portions 21 extending in the second direction F are formed as shown in FIG. 9A to FIG. 10C. As shown in FIG. 7A, in the shape-giving step, the protruding portions 51 of the first roll R1 and the depressions 52 of the second roll R2 mesh with each other, thereby shaping the non-woven fabric sheet 1 introduced into between the first roll R1 and the second roll R2.

In the shape-giving step, the first and/or second roll R1, R2 is preferably heated to a temperature range that is lower than the melting point of the constituent fibers 11 of the non-woven fabric sheet 1.

After the shape-giving step, the fusion-bonding step is performed as shown in FIG. 7B, wherein a portion of the shaped non-woven fabric sheet 1 is fusion-bonded while being sandwiched between the fusion-bond protruding portions 55 of the second roll R2 and the surface 53 of the third roll R3, thereby forming the fusion-bonded portions 22 (FIG. 8C) on the non-woven fabric sheet 1 of FIG. 8B, and obtaining the shaped sheet 2 of FIG. 8C. That is, the fusion-bonded portions 22, where the constituent fibers 11 of the non-woven fabric sheet 1 are fusion-bonded together, are formed along a part (e.g., FIG. 1) or whole (FIG. 4) of the periphery of the protruding portions 21 on the single-layer shaped sheet 2. As shown in FIG. 8C, the thickness of the fusion-bonded portions 22 of the single-layer shaped sheet 2 is smaller than the thickness of the protruding portions 21 of the single-layer shaped sheet 2.

Note that in the fusion-bonding step, the third roll R3 may be heated to a temperature range that is higher than the softening point of the thermoplastic resin of the constituent fibers 11 and is generally equal to the melting point thereof.

INDUSTRIAL APPLICABILITY

The present invention is applicable to various shaped sheets such as paper napkins as well as top sheets of disposable worn articles.

REFERENCE SIGNS LIST

1: Non-woven fabric sheet, 11: Constituent fibers
2: Shaped sheet, 20: Depressed portion, 21: Protruding portion
22: Fusion-bonded portion, 23: Central portion
D: First direction (width direction), F: Second dire n (longitudinal direction), V: Normal direction
R1, R2, R3: First to third rolls

The invention claimed is:
1. A shaped sheet including: a plurality of rows of protruding portions formed on a non-woven fabric sheet and extending in a first direction; and a plurality of rows of protruding portions formed on the non-woven fabric sheet and extending in a second direction that crosses the first direction, wherein:

the shaped sheet is more stretchable in the first direction than in the second direction;

the shaped sheet is formed from a single layer of the non-woven fabric sheet; and a fusion-bonded portion that extends discontinuously or continuously in the first direction and that has a smaller thickness than the protruding portions due to its fusion-bonded structure is provided along a part or whole of a periphery of the protruding portions on the shaped sheet.

2. The shaped sheet according to claim 1, wherein the fusion-bonded portion is formed by the fusion-bonded structure where constituent fibers of the single-layer non-woven fabric sheet are fusion-bonded together.

3. The shaped sheet according to claim 2, wherein the fusion-bonded portion is formed by the fusion-bonded structure that inhibits a stretch of the shaped sheet in the first direction.

4. The shaped sheet according to claim 1, wherein the fusion-bonded portion includes a central portion that is between two of the protruding portions that are adjacent to each other in the first direction, and the fusion-bonded portion extends at least in one direction along the first direction from the central portion.

5. The shaped sheet according to claim 1, a fiber density of constituent fibers is higher in the fusion-bonded portions than in the protruding portions.

6. The shaped sheet according to claim 1, a rate of elongation of the shaped sheet when pulled in the first direction is smaller in the fusion-bonded portions than in the protruding portions.

7. A method for manufacturing a shaped sheet including: a plurality of rows of protruding portions formed on a non-woven fabric sheet and extending in a first direction; and a plurality of rows of protruding portions formed on the non-woven fabric sheet and extending in a second direction that crosses the first direction, the method comprising:

a step of conveying a single layer of the non-woven fabric sheet in a longitudinal direction, the non-woven fabric sheet being more stretchable in a width direction than in the longitudinal direction;

a shape-giving step of shaping the plurality of rows of protruding portions on the non-woven fabric sheet being conveyed; and a fusion-bonding step of forming a fusion-bonded portion, where constituent fibers of the single-layer non-woven fabric sheet are fusion-bonded together, along a part or whole of a periphery of the protruding portions on the single-layer non-woven fabric sheet or the shaped sheet.

8. The manufacturing method according to claim 7, wherein:

in the shape-giving step, a first roll and a second roll mesh with each other, thereby shaping the non-woven fabric sheet;

in the shape-giving step, the first roll and/or the second roll are heated to a temperature range that is lower than a melting point of the constituent fibers of the non-woven fabric sheet; and the fusion-bonding step is performed as a heating device comes into contact with the second roll with the fusion-bonded portion of the non-woven fabric sheet interposed between the second roll and the heating device.

* * * * *